(12) United States Patent
Okakura et al.

(10) Patent No.: US 7,374,921 B2
(45) Date of Patent: May 20, 2008

(54) CELLULASE TOLERANT TO SURFACTANTS

(75) Inventors: Kaoru Okakura, Kanagawa (JP); Koji Yanai, Kanagawa (JP)

(73) Assignee: Meiji Seika Kaisha, Ltd., Tokyo (JP)

( * ) Notice: Subject to any disclaimer, the term of this patent is extended or adjusted under 35 U.S.C. 154(b) by 0 days.

(21) Appl. No.: 10/533,310

(22) PCT Filed: Oct. 31, 2003

(86) PCT No.: PCT/JP03/14013

§ 371 (c)(1),
(2), (4) Date: Apr. 29, 2005

(87) PCT Pub. No.: WO2004/039969

PCT Pub. Date: May 13, 2004

(65) Prior Publication Data
US 2006/0035361 A1    Feb. 16, 2006

(30) Foreign Application Priority Data
Oct. 31, 2002    (JP) .............................. 2002-318303

(51) Int. Cl.
C12N 9/42 (2006.01)
C12N 5/16 (2006.01)
C12Q 1/34 (2006.01)
C12P 21/06 (2006.01)
C07H 21/04 (2006.01)
C11D 3/00 (2006.01)
C07K 1/00 (2006.01)

(52) U.S. Cl. .................. 435/209; 435/18; 435/69.1; 435/320.1; 435/325; 510/320; 536/23.2; 530/350

(58) Field of Classification Search .............. 435/209, 435/18, 23.2, 252.3; 530/350
See application file for complete search history.

(56) References Cited

FOREIGN PATENT DOCUMENTS

WO    WO 98/12307        3/1998
WO    WO 01/90375 A1    11/2001

OTHER PUBLICATIONS

Shiarai, et al., "Crystal Structure of Alkaline Cellulase K: Insight Into The Alkaline Adaptation of an Industrial Enzyme", Journal of Molecular Biology, London, GB, vol. 310, No. 5, Jul. 27, 2001, pp. 1079-1087.

*Primary Examiner*—Ponnathapu Achutamurthy
*Assistant Examiner*—Iqbal Chowdhury
(74) *Attorney, Agent, or Firm*—Sughrue Mion, PLLC

(57) ABSTRACT

Disclosed is a novel cellulase having an amino acid sequence in which the 162nd and/or 166th amino acid residues in the amino acid sequence of cellulase NCE5 are substituted. Further, a polynucleotide encoding the novel cellulase, an expression vector containing the polynucleotide, a host cell transformed with the expression vector, and a cellulase preparation and a washing composition containing the cellulase are disclosed. The cellulase of the present invention is resistant to surfactants, and maintains a high activity even under alkaline conditions.

14 Claims, No Drawings

SEQUENCE LISTING

```
<160> NUMBER OF SEQ ID NOS: 8

<210> SEQ ID NO 1
<211> LENGTH: 205
<212> TYPE: PRT
<213> ORGANISM: Humicola insolens
<220> FEATURE:
<221> NAME/KEY: mat_peptide
<222> LOCATION: (1)..(205)

<400> SEQUENCE: 1

Gln Ser Gly Ser Gly Arg Thr Thr Arg Tyr Trp Asp Cys Cys Lys Pro
 1               5                  10                  15

Ser Cys Ala Trp Pro Gly Lys Gly Pro Ala Pro Val Arg Thr Cys Asp
             20                  25                  30

Arg Trp Asp Asn Pro Leu Phe Asp Gly Gly Asn Thr Arg Ser Gly Cys
         35                  40                  45

Asp Ala Gly Gly Gly Ala Tyr Met Cys Ser Asp Gln Ser Pro Trp Ala
     50                  55                  60

Val Ser Asp Asp Leu Ala Tyr Gly Trp Ala Ala Val Asn Ile Ala Gly
 65                  70                  75                  80

Ser Asn Glu Arg Gln Trp Cys Cys Ala Cys Tyr Glu Leu Thr Phe Thr
```

```
                    85                  90                  95
Ser Gly Pro Val Ala Gly Lys Arg Met Ile Val Gln Ala Ser Asn Thr
            100                 105                 110
Gly Gly Asp Leu Gly Asn Asn His Phe Asp Ile Ala Met Pro Gly Gly
            115                 120                 125
Gly Val Gly Ile Phe Asn Ala Cys Thr Asp Gln Tyr Gly Ala Pro Pro
            130                 135                 140
Asn Gly Trp Gly Gln Arg Tyr Gly Gly Ile Ser Gln Arg His Glu Cys
145                 150                 155                 160
Asp Ala Phe Pro Glu Lys Leu Lys Pro Gly Cys Tyr Trp Arg Phe Asp
            165                 170                 175
Trp Phe Leu Asn Ala Asp Asn Pro Ser Val Asn Trp Arg Gln Val Ser
            180                 185                 190
Cys Pro Ala Glu Ile Val Ala Lys Ser Gly Cys Ser Arg
            195                 200                 205

<210> SEQ ID NO 2
<211> LENGTH: 615
<212> TYPE: DNA
<213> ORGANISM: Humicola insolens

<400> SEQUENCE: 2
cagtccggca gcggccgcac cacgcgctac tgggactgct gcaagccgtc gtgcgcgtgg      60
cccggcaagg gccggcgcc cgtgcggacg tgcgaccggt gggacaaccc gctgttcgac     120
ggcggcaaca cgcgcagcgg gtgcgacgcg ggcggcggcg cctacatgtg ctcggaccag     180
agcccgtggg cggtcagcga cgacctggcg tacggctggg cggccgtcaa cattgccggc     240
tccaacgaga ggcagtggtg ctgcgcctgc tacgagctga ccttcaccag cgggccggtg     300
gcgggcaaga ggatgattgt gcaggcgagc aacacgggag gcgatttggg gaacaaccac     360
tttgatattg ctatgcccgg cggtggcgtc ggtatcttca acgcctgcac cgaccagtac     420
ggcgcgcccc ccaacggctg gggccagcgc tacgcggca tcagccaacg ccacgagtgc     480
gacgccttcc ccgagaagct caagcccggc tgctactggc gctttgactg gttcctcaac     540
gccgacaacc cgagcgtcaa ctggcggcag gtcagctgcc cggccgagat tgtggccaag     600
agcggctgct cgcgt                                                    615

<210> SEQ ID NO 3
<211> LENGTH: 205
<212> TYPE: PRT
<213> ORGANISM: Artificial Sequence
<220> FEATURE:
<223> OTHER INFORMATION: A detergent-resistant cellulase

<400> SEQUENCE: 3

Gln Ser Gly Ser Gly Arg Thr Thr Arg Tyr Trp Asp Cys Cys Lys Pro
1               5                   10                  15
Ser Cys Ala Trp Pro Gly Lys Gly Pro Ala Pro Val Arg Thr Cys Asp
            20                  25                  30
Arg Trp Asp Asn Pro Leu Phe Asp Gly Gly Asn Thr Arg Ser Gly Cys
            35                  40                  45
Asp Ala Gly Gly Gly Ala Tyr Met Cys Ser Asp Gln Ser Pro Trp Ala
            50                  55                  60
Val Ser Asp Asp Leu Ala Tyr Gly Trp Ala Ala Val Asn Ile Ala Gly
65                  70                  75                  80
Ser Asn Glu Arg Gln Trp Cys Cys Ala Cys Tyr Glu Leu Thr Phe Thr
```

```
                85                  90                  95
Ser Gly Pro Val Ala Gly Lys Arg Met Ile Val Gln Ala Ser Asn Thr
            100                 105                 110
Gly Gly Asp Leu Gly Asn Asn His Phe Asp Ile Ala Met Pro Gly Gly
            115                 120                 125
Gly Val Gly Ile Phe Asn Ala Cys Thr Asp Gln Tyr Gly Ala Pro Pro
            130                 135                 140
Asn Gly Trp Gly Gln Arg Tyr Gly Gly Ile Ser Gln Arg His Glu Cys
145                 150                 155                 160
Asp Pro Phe Pro Glu Lys Leu Lys Pro Gly Cys Tyr Trp Arg Phe Asp
            165                 170                 175
Trp Phe Leu Asn Ala Asp Asn Pro Ser Val Asn Trp Arg Gln Val Ser
            180                 185                 190
Cys Pro Ala Glu Ile Val Ala Lys Ser Gly Cys Ser Arg
            195                 200                 205

<210> SEQ ID NO 4
<211> LENGTH: 205
<212> TYPE: PRT
<213> ORGANISM: Artificial Sequence
<220> FEATURE:
<223> OTHER INFORMATION: A detergent-resistant cellulase

<400> SEQUENCE: 4

Gln Ser Gly Ser Gly Arg Thr Thr Arg Tyr Trp Asp Cys Cys Lys Pro
1               5                   10                  15
Ser Cys Ala Trp Pro Gly Lys Gly Pro Ala Pro Val Arg Thr Cys Asp
            20                  25                  30
Arg Trp Asp Asn Pro Leu Phe Asp Gly Gly Asn Thr Arg Ser Gly Cys
            35                  40                  45
Asp Ala Gly Gly Gly Ala Tyr Met Cys Ser Asp Gln Ser Pro Trp Ala
            50                  55                  60
Val Ser Asp Asp Leu Ala Tyr Gly Trp Ala Ala Val Asn Ile Ala Gly
65                  70                  75                  80
Ser Asn Glu Arg Gln Trp Cys Cys Ala Cys Tyr Glu Leu Thr Phe Thr
            85                  90                  95
Ser Gly Pro Val Ala Gly Lys Arg Met Ile Val Gln Ala Ser Asn Thr
            100                 105                 110
Gly Gly Asp Leu Gly Asn Asn His Phe Asp Ile Ala Met Pro Gly Gly
            115                 120                 125
Gly Val Gly Ile Phe Asn Ala Cys Thr Asp Gln Tyr Gly Ala Pro Pro
            130                 135                 140
Asn Gly Trp Gly Gln Arg Tyr Gly Gly Ile Ser Gln Arg His Glu Cys
145                 150                 155                 160
Asp Ala Phe Pro Glu Glu Leu Lys Pro Gly Cys Tyr Trp Arg Phe Asp
            165                 170                 175
Trp Phe Leu Asn Ala Asp Asn Pro Ser Val Asn Trp Arg Gln Val Ser
            180                 185                 190
Cys Pro Ala Glu Ile Val Ala Lys Ser Gly Cys Ser Arg
            195                 200                 205

<210> SEQ ID NO 5
<211> LENGTH: 205
<212> TYPE: PRT
<213> ORGANISM: Artificial Sequence
<220> FEATURE:
<223> OTHER INFORMATION: A detergent-resistant cellulase
```

<400> SEQUENCE: 5

Gln Ser Gly Ser Gly Arg Thr Thr Arg Tyr Trp Asp Cys Cys Lys Pro
1               5                   10                  15
Ser Cys Ala Trp Pro Gly Lys Gly Pro Ala Pro Val Arg Thr Cys Asp
            20                  25                  30
Arg Trp Asp Asn Pro Leu Phe Asp Gly Gly Asn Thr Arg Ser Gly Cys
        35                  40                  45
Asp Ala Gly Gly Gly Ala Tyr Met Cys Ser Asp Gln Ser Pro Trp Ala
    50                  55                  60
Val Ser Asp Asp Leu Ala Tyr Gly Trp Ala Ala Val Asn Ile Ala Gly
65                  70                  75                  80
Ser Asn Glu Arg Gln Trp Cys Cys Ala Cys Tyr Glu Leu Thr Phe Thr
                85                  90                  95
Ser Gly Pro Val Ala Gly Lys Arg Met Ile Val Gln Ala Ser Asn Thr
            100                 105                 110
Gly Gly Asp Leu Gly Asn Asn His Phe Asp Ile Ala Met Pro Gly Gly
        115                 120                 125
Gly Val Gly Ile Phe Asn Ala Cys Thr Asp Gln Tyr Gly Ala Pro Pro
    130                 135                 140
Asn Gly Trp Gly Gln Arg Tyr Gly Gly Ile Ser Gln Arg His Glu Cys
145                 150                 155                 160
Asp Pro Phe Pro Glu Glu Leu Lys Pro Gly Cys Tyr Trp Arg Phe Asp
                165                 170                 175
Trp Phe Leu Asn Ala Asp Asn Pro Ser Val Asn Trp Arg Gln Val Ser
            180                 185                 190
Cys Pro Ala Glu Ile Val Ala Lys Ser Gly Cys Ser Arg
        195                 200                 205

<210> SEQ ID NO 6
<211> LENGTH: 27
<212> TYPE: DNA
<213> ORGANISM: Artificial Sequence
<220> FEATURE:
<223> OTHER INFORMATION: A primer for site-directed mutagenesis

<400> SEQUENCE: 6
ggggaagggg tcgcactcgt ggcgttg                                      27

<210> SEQ ID NO 7
<211> LENGTH: 27
<212> TYPE: DNA
<213> ORGANISM: Artificial Sequence
<220> FEATURE:
<223> OTHER INFORMATION: A primer for site-directed mutagenesis

<400> SEQUENCE: 7
cttgagctcc tcggggaagg cgtcgca                                      27

<210> SEQ ID NO 8
<211> LENGTH: 30
<212> TYPE: DNA
<213> ORGANISM: Artificial Sequence
<220> FEATURE:
<223> OTHER INFORMATION: A primer for site-directed mutagenesis

<400> SEQUENCE: 8
gagctcctcg gggaaggggt cgcactcgtg                                   30

CELLULASE TOLERANT TO SURFACTANTS

TECHNICAL FIELD

The present invention relates to a novel cellulase having an amino acid sequence wherein a partial amino acid sequence is substituted in the sequence of the original cellulase consisting of the amino acid sequence of SEQ ID NO: 1.

BACKGROUND ART

Cellulases are utilized, based on their properties, in various industrial fields, particularly the field of fabric processing. In this field, a cellulose-containing fabric is treated with cellulase to impart desired properties to the fabric. For example, a treatment with cellulase is carried out to improve the touch and/or appearance of cellulose-containing fabric, or for a "biowash" which imparts a "stonewash" appearance to a colored cellulose-containing fabric, thereby providing the fabric with localized color variations. Further, in the process for manufacturing lyocell, cellulase is used for removing the fuzz generated in the process from the fabric surface. In this connection, lyocell is a regenerated cellulose fabric derived from wood pulp, and has recently attracted attention for properties (such as high strength or water absorption) and as a production process that causes less environmental pollution.

Hitherto, it has been considered that cellulase decomposes cellulose by the synergistic effect of plural enzymes. Because of an evolution of protein separation techniques or genetic engineering techniques, an attempt has been carried out to separate enzyme components appropriate for fabric processing from cellulase consisting of plural enzymes, and to produce the enzyme components. Particularly, cellulases derived from microorganisms belonging to filamentous fungi such as genus *Trichoderma* or genus *Humicola* have been subjected to serious study. For example, as cellulase components, CBH I, EG V, NCE4, and NCE2 in genus *Humicola*, and CBH I, CBH II, EG II, and EG III in genus *Trichoderma* were isolated, and thus, cellulase preparations containing as the major components one or more specific cellulase components appropriate for each purpose can be produced by preparing overexpressed enzymes or mono-component enzymes using genetic engineering techniques.

Further, it is known that endoglucanase enzyme NCE5 is useful in imparting a stonewash appearance to stained cellulose containing fiber or improving the touch thereof, as a cellulase which causes a slight redeposition or backstaining (i.e., a slight back staining) of an indigo dye to clothing during the treatment (see patent reference 1).

In another aspect, when cellulases are used as a detergent for clothing, not only a quantitative improvement of cellulase components used but also a qualitative one is desired. More particularly, a detergent for clothing contains various surfactants, and a solution obtained by solubilizing the detergent for clothing in water is alkaline (pH10 to pH11). Therefore, it is necessary that cellulases contained in a detergent for clothing should be resistant to various surfactants, and exhibit a strong activity under alkaline conditions.
(patent reference 1) International Publication WO01/90375 (pages 2-3, and the sequence of SEQ ID NO: 1 in the Sequence Listing)

DISCLOSURE OF THE INVENTION

An object of the present invention is to provide a novel cellulase resistant to surfactants and/or having a high activity under alkaline conditions.

The present inventors conducted intensive studies, and as a result, successfully obtained a novel cellulase resistant to surfactants and/or having a high activity under alkaline conditions, by substituting the 162nd and/or 166th amino acid residues with different amino acid residues in the amino acid sequence of a cellulase (NCE5) consisting of the amino acid sequence of SEQ ID NO: 1. The present invention relates to:

[1] a cellulase having (1) an amino acid sequence in which a 162nd amino acid residue and/or a 166th amino acid residue in the amino acid sequence of SEQ ID NO: 1 are substituted, or (2) an amino acid sequence in which one or plural amino acids are added to or deleted from the N-terminus of the amino acid sequence (1);

[2] the cellulase of [1] having the amino acid sequence of SEQ ID NO: 3;

[3] the cellulase of [1], wherein the 166th amino acid is substituted with glutamic acid or aspartic acid;

[4] the cellulase of [3] having the amino acid sequence of SEQ ID NO: 4;

[5] a cellulase having the amino acid sequence of SEQ ID NO: 5;

[6] a polynucleotide encoding the cellulase of [1] to [5];

[7] an expression vector comprising the polynucleotide of [6];

[8] a host cell transformed with the expression vector of [7];

[9] a process for producing the cellulase of [1] to [5], comprising the steps of:
cultivating the host cell of [8], and
collecting the cellulase from the host cell and/or culture obtained by the cultivation;

[10] a cellulase preparation comprising the cellulase of [1] to [5];

[11] a washing composition comprising the cellulase of [1] to [5] or the cellulase preparation of [10];

[12] a method of treating a cellulose-containing fabric, comprising the step of bringing the cellulose-containing fabric into contact with the cellulase of [1] to [5], the cellulase preparation of [10], or the washing composition of [11];

[13] a method of reducing fuzzing of a cellulose-containing fabric or reducing a rate of the formation of fuzz, comprising the step of bringing the cellulose-containing fabric into contact with the cellulase of [1] to [5], the cellulase preparation of [10], or the washing composition of [11];

[14] a method of reducing weight to improve the touch and appearance of a cellulose-containing fabric, comprising the step of bringing the cellulose-containing fabric into contact with the cellulase of [1] to [5], the cellulase preparation of [10], or the washing composition of [11];

[15] a method of color clarification of a colored cellulose-containing fabric, comprising the step of bringing the colored cellulose-containing fabric into contact with the cellulase of [1] to [5], the cellulase preparation of [10], or the washing composition of [11];

[16] a method of providing a localized color variation to a colored cellulose-containing fabric, comprising the step of bringing the colored cellulose-containing fabric into contact with the cellulase of [1] to [5], the cellulase preparation of [10], or the washing composition of [11];

[17] a method of reducing stiffness of a cellulose-containing fabric or reducing a rate of the formation of stiffness, comprising the step of bringing the cellulose-containing fabric into contact with the cellulase of [1] to [5], the cellulase preparation of [10], or the washing composition of [11];

[18] the method of [12] to [17], wherein the treatment of the fabric is carried out by soaking, washing, or rinsing the fabric;

[19] a method of deinking waste paper, comprising the step of treating the waste paper with the cellulase of [1] to [5] or the cellulase preparation of [10] together with a deinking agent;

[20] a method of improving a freeness of paper pulp, comprising the step of treating the paper pulp with the cellulase of [1] to [5] or the cellulase preparation of [10]; and

[21] a method of improving a digestibility of animal feed, comprising the step of treating the animal feed with the cellulase of [1] to [5] or the cellulase preparation of [10].

The term "polynucleotide" as used herein includes DNA and RNA.

BEST MODE FOR CARRYING OUT THE INVENTION

The present invention will be explained in detail hereinafter.

Original Cellulase

The term "original cellulase" as used herein means a cellulase consisting of the amino acid sequence of SEQ ID NO: 1. Further, a secretory signal sequence is sometimes processed differently, depending on a host used for producing the original cellulase. Therefore, a homologous protein having an amino acid sequence in which one or plural amino acids are added to or deleted from the N-terminus of the amino acid sequence of SEQ ID NO: 1 is included in the original cellulase.

Novel Cellulase of the Present Invention

As the novel cellulase in the present invention, when the original cellulase consists of the amino acid sequence of SEQ ID NO: 1, there may be mentioned, for example, a cellulase having an amino acid sequence in which one or two amino acid residues selected from the group consisting of the 162nd amino acid and the 166th amino acid in the amino acid sequence of SEQ ID NO: 1 are substituted with different amino acid residues. Further, a cellulase obtained from an isolated naturally-occurring strain is included in the cellulase of the present invention, so long as the 162nd and/or 166th amino acids in the amino acid sequence of SEQ ID NO: 1, or the corresponding amino acid(s) are substituted.

As the cellulase of the present invention, a cellulase having an amino acid sequence in which the 162nd amino acid in the amino acid sequence of SEQ ID NO: 1 is substituted with proline and the 166th amino acid therein is substituted with glutamic acid or aspartic acid, is preferable. Further, a cellulase having the amino acid sequence of SEQ ID NOS: 3 to 5 is more preferable. The cellulases exhibit advantageous features, that is, resistance to a surfactant and/or maintaining a high activity under alkaline conditions.

As the novel cellulase in the present invention, when the original cellulase is a homologous protein of the cellulase having the amino acid sequence of SEQ ID NO: 1, there may be mentioned, for example, a cellulase having an amino acid sequence in which one or two amino acid residues selected from the group consisting of amino acids corresponding to the 162nd amino acid and the 166th amino acid in the amino acid sequence of SEQ ID NO: 1 are substituted with different amino acid residues. In this connection, the amino acid residues to be substituted in the homologous protein may be easily selected by comparing amino acid sequences using a known algorithm.

Generation of Novel Cellulase of the Present Invention

The novel cellulase of the present invention may be generated, for example, by recombinant DNA techniques or polypeptide synthesis techniques, or obtained from an isolated naturally-occurring strain.

When the recombinant DNA techniques are used, the novel cellulase of the present invention may be prepared, for example, by the following procedures. A DNA encoding an original cellulase is obtained, and a site-directed mutagenesis is carried out in the obtained DNA to substitute the desired amino acid(s). A host cell is transformed with an expression vector comprising the mutated DNA, and the transformant is cultivated to prepare the novel cellulase. The DNA encoding an original cellulase may be completely synthesized on the basis of the amino acid sequence of SEQ ID NO: 1 in consideration of a host cell used, and may be preferably a DNA consisting of the nucleotide sequence of SEQ ID NO: 2, which may be obtained from a cDNA library of *Humicola insolens* in accordance with conventional methods used in genetic engineering.

Some methods for introducing a mutation into a specific site of a gene, such as a gapped duplex method [Methods in Enzymolog 154, 350(1987)] or a Kunkel method [Methods in Enzymology, 154, 367(1987)], are known to those skilled in the art. These methods may be used for carrying out a site-directed mutagenesis in the DNA encoding an original cellulase. The nucleotide sequence of the mutated DNA may be confirmed by, for example, a Maxam-Gilbert chemical modification method [Methods in Enzymology, 65, 499 (1980)] or a dideoxinucleotide chain termination method [Gene, 19, 269(1982)]. The amino acid sequence of the cellulase of the present invention may be confirmed on the basis of the obtained nucleotide sequence.

Production of Novel Cellulase of the Present Invention

The cellulase of the present invention may be produced in a host cell by transforming the host cell with a DNA fragment encoding the cellulase in the form of a DNA molecule (particularly an expression vector) so that the DNA fragment may be replicated and expressed in the host cell.

According to the present invention, an expression vector comprising a DNA fragment encoding the cellulase of the present invention, so that the DNA fragment may be replicated and the protein encoded by the DNA fragment may be expressed in a host microorganism, is provided. The expression vector of the present invention can be constructed on the basis of a self-replicating vector (such as a plasmid), which exists as an extrachromosomal element and can replicate independently of the replication of chromosomes. Alternatively, the expression vector of the present invention may be a vector which is integrated into the genome of the host microorganism and replicated together with chromosomes, when the host is transformed with the vector. The construction of the vector of the present invention can be carried out by ordinary procedures or methods commonly used in genetic engineering.

To express a protein having a desired activity by transforming a host microorganism with the expression vector, it is preferable that the expression vector contains, for example, a DNA sequence capable of controlling the expression, or a genetic marker to select transformants, in addition to the DNA fragment of the present invention. The DNA sequence capable of controlling the expression includes, for example, a promoter, a terminator, or a DNA sequence encoding a signal peptide for secretion. The promoter is not particularly limited, so long as it shows a transcriptional activity in a host microorganism. The promoter can be obtained as a DNA sequence which controls the expression of a gene encoding a protein the same as or different from that derived from the host microorganism. The signal peptide is not particularly limited, so long as it contributes to the protein secretion in a host microorganism. The signal peptide can be obtained as a DNA sequence derived from a gene encoding a protein the same as or different from that derived from the host microorganism. The genetic marker can be appropriately selected in accordance with the method for selecting a transformant. As the genetic marker, for example, a drug resistance gene or a gene complementing an auxotrophic mutation can be used.

According to the present invention, a microorganism transformed with the expression vector is provided. A host-vector system which can be used in the present invention is not particularly limited. For example, a system utilizing *E. coli*, *Actinomycetes*, yeasts, or filamentous fungi, or a system for the expression of a fusion protein using such a microorganism can be used. Transformation of a microorganism with the expression vector can be carried out in accordance with an ordinary method in the art.

The transformant of the present invention is cultivated in an appropriate medium, and the resulting culture is used to obtain the isolated protein of the present invention. According to the present invention, a process for producing the novel protein of the present invention can be provided. The transformant can be cultivated under the conditions commonly used in the cultivation thereof. Further, after the cultivation, the protein of interest can be collected in accordance with an ordinary method in the art.

Use of Novel Cellulase of the Present Invention/Cellulase Preparation of the Present Invention The present invention relates to a cellulase preparation comprising the cellulase of the present invention.

Conventionally, the cellulase preparation may contain, for example, fillers (for example, lactose, sodium chloride, or sorbitol), antiseptics, and/or nonionic surfactants, in addition to the cellulase enzyme. The form of the cellulase preparation may be solid or liquid, such as powder, particulate, granule, non-dusting granule, or liquid formulation. In addition to the cellulase of the present invention, the cellulase preparation of the present invention may contain other cellulase enzymes, such as cellobiohydrolase, β-gulucosidase, or endoglucanase other than the endoglucanase of the present invention.

The non-dusting granule (preferably a granule not having a dustability), that is one form of cellulase preparation, can be produced according to the common dry granulation method. That is, powder cellulase is mixed with one or plural substances selected from the group comprising inorganic salts such as sodium sulfate or sodium chloride which are neutral and do not have an effect on the endoglucanase activity; minerals such as bentonite or montmorillonite which do not have an effect on the endoglunanase activity; and neutral organic substances such as starch or powder cellulase. Thereafter, the powders or the finely suspended suspension of one or plural nonionic surfactants are added to the mixture, and then the obtained product is fully mixed or kneaded. Depending on the situation, a synthetic polymer such as polyethylene glycol or a natural polymer such as starch, which binds solids, is optionally added to the mixture and further kneaded. Thereafter, granulation is carried out by extrusion molding, using, for example, a disk pelleter, and the obtained molded material is then converted into a spherical form using a marumerizer followed by drying, so that non-dusting granules can be produced. The amount of one or plural nonionic surfactants is not particularly limited, and is preferably 0.1 to 50% by weight, more preferably 0.1 to 30% by weight, most preferably 0.1 to 10% by weight to the total weight of the cellulase preparation of the present invention. It is also possible to coat the surface of granules with a polymer or the like to control the permeation of oxygen or water.

Further, the liquid preparation, which is one of the cellulase preparations (preferably stabilized liquid), can be prepared by blending an endoglucanase stabilizer (such as a synthetic or natural polymer) with a solution containing the cellulase of the present invention and, if necessary, adding inorganic salts and/or a synthetic preservative. In this case, one or plural nonionic surfactants can be blended with the liquid preparation. The amount of one or plural of the nonionic surfactants is not particularly limited, and is preferably 0.1 to 50% by weight, more preferably 0.1 to 30% by weight, most preferably 0.1 to 10% by weight to the total amount of the cellulase preparation of the present invention.

Further, the present invention provides a washing composition comprising the cellulase of the present invention or the cellulase preparation of the present invention. The washing composition may also comprise surfactants which may be anionic, nonionic, cationic, amphoteric or zwitterionic, or a mixture thereof. The washing composition may comprise other washing compositions known in the art, for example, a builder, bleach, bleaching agent, tarnish inhibitor, sequestant, soil releasing polymer, flavor, other enzymes (such as protease, lipase, or amylase), stabilizer for enzyme, granulater, optical brightner, and/or foaming agent. As typical anionic surfactants, there may be mentioned, for example, linear alkyl benzene sulfonate (LAS), alkyl sulphate (AS), α-olefin sulfonate (AOS), polyoxyethylene alkylether sulfonate (AES), α-sulfo fatty acid ester (α-SFMe), or alkali metal salts of naturally-occurring fatty acid. As the nonion surfactants, there may be mentioned, for example, polyoxyethylene alkyl ether (AE), alkylpolyethylene glycol ether, nonylphenol polyethylene glycol ether, fatty acid methyl ester ethoxylate, sucrose, or fatty acid ester of glucose, or esters of alkylglucoside or polyethoxylated alkylglucoside.

The method of the present invention for treating a cellulose-containing fabric is carried out by bringing the cellulose-containing fabric into contact with the cellulase of the present invention, the cellulase preparation of the present invention, or the washing composition of the invention.

The following properties of cellulose-containing fabric can be improved by the method of the present invention:
(1) Removal of fuzz (reduction of the rate of the formation of fuzz, and reduction of fuzz);
(2) Improvement of the touch and appearance of a fabric by reducing weight;
(3) Color clarification of a colored cellulose-containing fabric;
(4) Providing a localized color variation to a colored cellulose-containing fabric, that is, providing a stonewash-like appearance and texture to a colored cellulose-containing fabric, typically jeans; and
(5) Softening of a fabric (reduction of the rate of stiffness, and a reduction of stiffness).

More particularly, the method of the present invention can be carried out by adding the cellulase of the present invention, the cellulase preparation of the present invention, or the washing composition of the present invention into water in which a fabric is or will be soaked, for example, during a soaking, washing, or rinsing of a fabric.

Conditions such as contact temperature or the amount of the cellulose, the cellulase preparation, or the washing composition may be appropriately determined in accordance with various other conditions. For example, when reducing the rate of the formation of fuzz or reducing fuzzing of the cellulose-containing fabric, the cellulase, the cellulase preparation, or the washing composition in a protein concentration of 0.01 to 20 mg/L is preferably used at a temperature of approximately 10 to 60° C.

In a processing of reducing weight to improve the touch and appearance of the cellulose-containing fabric, the cellulase, the cellulase preparation, or the washing composition in a protein concentration of 0.1 to 50 mg/L is preferably used at a temperature of approximately 10 to 60° C.

When clarifying the color of the colored cellulose-containing fabric, the cellulase, the cellulase preparation, or the washing composition in a protein concentration of 0.01 to 20 mg/L is preferably used at a temperature of approximately 10 to 60° C.

When providing a localized color variation to a colored cellulose-containing fabric, the cellulase, the cellulase preparation, or the washing composition in a protein concentration of 0.1 to 100 mg/L is preferably used at a temperature of approximately 20 to 60° C.

When reducing the stiffness of a cellulose-containing fabric or reducing the rate of the formation of stiffness, the cellulase, the cellulase preparation, or the washing composition in a protein concentration of 0.01 to 20 mg/L is preferably used at a temperature of 10 to 60° C.

Further, the present invention relates to a method for deinking waste paper, characterized by using the cellulase of the present invention or the cellulase preparation of the present invention, in the process of treating the waste paper together with a deinking agent.

The cellulase or the cellulase preparation of the present invention is useful in the process of producing recycled paper from waste paper, since an efficiency of the deinking can be improved by reacting waste paper therewith. According to the deinking method, the whiteness of waste paper can be improved by remarkably reducing residual-ink fabric.

The deinking agent is not particularly limited, so long as it is agent which can be used in deinking waste paper in general. As the deinking agent, there may be mentioned, for example, alkalis (such as sodium hydroxide or sodium carbonate), sodium silicate, hydrogen peroxide, phosphates, anionic or nonionic surfactants, scavengers such as oleic acid, and assistant agents such as a pH stabilizer, a chelating agent, or a dispersing agent.

Waste paper which can be treated by the deinking method is not particularly limited, so long as it is common waste paper. As the waste paper, there may be mentioned, used newspaper, used magazine paper, and low to middle grade printed used paper which comprises mechanical pulp and chemical pulp; used wood-free paper comprising chemical pulp; or printed waste paper thereof such as coating paper. A paper other than the common waste paper can be treated by the deinking method, so long as it deposits ink.

Further, the present invention relates to a method for improving a freeness of paper pulp, which comprises the process of treating a paper pulp with the cellulase of the present invention or the cellulase preparation of the present invention.

According to the method, it is considered that this method can significantly improve a freeness of paper pulp, without a decline of strength. A paper pulp which can be treated by the method is not particularly limited, but there may be mentioned, for example, waste paper pulp, recycled paperboard pulp, kraft pulp, sulfite pulp, thermo-mechanical treatment pulp, and other high-yield pulp.

Further, the present invention relates to a method for improving a digestibility of animal feed, comprising the step of treating the animal feed with the cellulase of the present invention or the cellulase preparation of the present invention. According to this method, a digestibility of animal feed can be improved by digesting glucan in animal feed into appropriate molecules having a low molecular weight.

Further, a digestibility of glucan in animal feed can be improved by using the cellulase of the present invention in animal feed. According to the present invention, a method for improving a digestibility of animal feed, comprises the step of treating the animal feed with the cellulase of the present invention or the cellulase preparation of the present invention.

As shown above, the cellulase and the washing composition of the present invention and the method of the present invention using the same have been described. International Publication WO01/90375 discloses that an original cellulase of the present invention, cellulase NCE5, can be used as an active ingredient of the cellulase preparation or the washing composition; that cellulase NCE5 or a cellulase preparation or washing composition containing cellulase NCE5 can improve various properties of a cellulose-containing fabric [for example, removal of fuzz (such as, a reduction of the rate of the formation of fuzz, and reduction of fuzz); improvement of the touch and appearance of a fabric by reducing weight; color clarification of a colored cellulose-containing fabric; providing a localized color variation to a colored cellulose-containing fabric; or softening of a fabric (such as, reduction of the rate of the stiffness, and reduction of stiffness)]; that cellulase NCE5 or a cellulase preparation or washing composition containing cellulase NCE5 can deink waste paper; that cellulase NCE5 or a cellulase preparation or washing composition containing cellulase NCE5 can improve a freeness of paper pulp; and that cellulase NCE5 or a cellulase preparation or washing composition containing cellulase NCE5 can improve a digestibility of animal feed. The cellulase of the present invention exhibits an excellent resistance to surfactants and alkaline conditions, compared with the original cellulase NCE5. Therefore, it can be expected that advantageous effects may be obtained when the cellulase is used in the above methods using cellulase NCE5, or used as an active ingredient of the cellulase preparation or washing composition, instead of NCE5.

Deposition of Microorganism

*Escherichia coli* JM109 transformed with plasmid pNCE5Bam comprising a DNA which encodes an original cellulase of the present invention was domestically deposited (FERM BP-7138) in the International Patent Organism Depositary National Institute of Advanced Industrial Science and Technology [(Former Name) National Institute of Bioscience and Human-Technology Agency of Industrial Science and Technology (Address: AIST Tsukuba Central 6, 1-1, Higashi 1-chome Tukuba-shi, Ibaraki-ken 305-8566 Japan)] on Apr. 18, 2000.

*Humicola insolens* FERM BP-5977, which was used in Example 2(2), was domestically deposited (FERM P-15736) in the International Patent Organism Depositary National Institute of Advanced Industrial Science and Technology on Jul. 15, 1996, and was transferred to an international deposit (FERM BP-5977) on Jun. 13, 1997.

EXAMPLES

The present invention now will be further illustrated by, but is by no means limited to, the following Examples.

All changes and modifications not mentioned in the present specification but obvious to those skilled in the art are herein incorporated by reference.

Example 1

Construction of Genes Encoding Cellulases

DNAs encoding a cellulase [hereafter referred to as A162P (SEQ ID NO: 3)] in which the 162nd amino acid of the original cellulase consisting of the amino acid sequence of SEQ ID NO: 1 was substituted with proline, a cellulase [hereafter referred to as K166E (SEQ ID NO: 4)] in which the 166th amino acid thereof was substituted with glutamic acid, and a cellulase [hereafter referred to as APKE (SEQ ID NO: 5)] in which the 162nd and 166th amino acids thereof were substituted with proline and glutamic acid, respectively, were constructed in accordance with the following procedures.

The desired site-directed mutations were introduced into a DNA encoding the original cellulase by using plasmid pNCE5Bam (WO 01/90375) as a template DNA, and LA PCR in vitro Mutagenesis Kit (Takara Shuzo), in accordance with a protocol attached to the kit. Three primers were used for the site-directed mutagenesis.

```
                                        (SEQ NO: 6)
NCE5-A162P:  5'-GGGGAAGGGGTCGCACTCGTGGCGTTG-3'

(SEQ NO: 7)
NCE5-K166E:  5'-CTTGAGCTCCTCGGGGAAGGCGTCGCA-3'

(SEQ NO: 8)
NCE5-APKE:   5'-GAGCTCCTCGGGGAAGGGGTCGCACTCGTG-3'
```

The primers NCE5-A162P, NCE5-K166E, and NCE5-APKE are primers for generating the DNAs which encode the cellulases A162P, K166E, and APKE, respectively.

The mutation-introduced PCR products obtained by using the three primers were digested with restriction enzymes EcoRI and PstI, and extracted with phenol:chloroform: isoamyl alcohol (25:24:1), and then ethanol precipitation was carried out. Each DNA fragment was ligated to plasmid pUC118 previously digested with restriction enzymes EcoRI and PstI, to obtain plasmids pNCE5AP-118(A162P), pNCE5KE-118 (K166E), and pNCE5APKE-118 (APKE). The nucleotide sequence of each fragment inserted in the three plasmids was determined by a fluorescent DNA sequencer (ABI PRISM 310 Genetic Analyzer; Perkin-Elmer) to confirm that only the desired mutations were introduced into the DNA fragments.

Example 2

Expression of each Cellulase Gene in *Humicola insolens*

(1) Construction of Plasmids for Expressing Cellulase Genes

The plasmids pNCE5AP-118, pNCE5KE-118, and pNCE5APKE-118 comprising each cellulase gene obtained in Example 1 were digested with restriction enzyme BamHI, and were subjected to agarose gel electrophoresis to collect three DNA fragments of approximately 0.7 kbp. Each DNA fragment was ligated to expression vector pJD-c5 (WO 01/90375) for *Humicola insolens* FERM BP-5977, which was previously digested with restriction enzyme BamHI and dephosphorylated with alkaline phosphatase (Takara Shuzo) derived from *E. coli*, to obtain plasmids pNCE5AP(A162P), pNCE5KE(K166E), and pNCE5APKE(APKE) for expressing each cellulase gene.

(2) Transformation of *Humicola insolens* FERM BP-5977

*Humicola insolens* FERM BP-5977 was cultivated in an (S) medium at 37° C. for 24 hours, and collected by centrifugation at 3000 rpm for 10 min. The (S) medium was prepared by removing avicel from a (N) medium (5.0% avicel, 2.0% yeast extract, 0.1% peptone, 0.03% calcium chloride, 0.03% magnesium chloride, pH 6.8) and adding glucose (3.0%) thereto. The resulting mycelia were washed with 0.5 mol/L sucrose, and suspended in 10 mL of an enzyme solution for generating protoplasts (3 mg/mL glucuronidase, 1 mg/mL Chitinase, 1 mg/mL Zymolyase, and 0.5 mol/L sucrose) previously filtrated with a filter (0.45 μm). The suspension was shaken at 30° C. for 60 to 90 minutes to generate protoplasts. The suspension was filtrated, and centrifuged at 2500 rpm for 10 minutes to collect protoplasts. The protoplasts were washed with an SUTC buffer [0.5 mol/L sucrose, 10 mmol/L calcium chloride, and 10 mmol/L Tris-HCl (pH 7.5)].

The protoplasts were suspended in 1 mL of the SUTC buffer. To 100 μL of the suspension, 10 μg of each DNA (TE) solution (10 μL) was added, and allowed to stand on ice for 5 minutes. Further, 400 μL of a PEG solution [60% PEG4000, 10 mmol/L calcium chloride, and 10 mmol/L Tris-HCl (pH 7.5)] was added, and allowed to stand on ice for 20 minutes. After 10 mL of the SUTC buffer was added, the whole was centrifuged at 2500 rpm for 10 minutes. The collected protoplasts were suspended in 1 mL of the SUTC buffer, centrifuged at 4000 rpm for 5 minutes, and finally suspended in 100 μL of the SUTC buffer.

The protoplasts treated as above were overlaid with YMG [1% glucose, 0.4% yeast extract, 0.2% malt extract, and 1% agar (pH 6.8)] soft agar on a YMG medium containing hygromycin (200 μg/mL), and incubated at 37° C. for 5 days to obtain transformants as colonies.

(3) Evaluation of Transformants by SDS-PAGE

*Humicola insolens* transformants obtained by using plasmids pNCE5AP, pNCE5KE, and pNCE5APKE were cultivated in the (N) medium (5.0% avicel, 2.0% yeast extract, 0.1% peptone, 0.03% calcium chloride, 0.03% magnesium chloride, pH 6.8) at 37° C. for 5 days, and the resulting culture supernatants were analyzed by SDS-PAGE.

The SDS-PAGE was carried out by using a Tefco system composed of a tank for electrophoresis (No. 03-101), a power supply (Model: 3540), 12% gel (01-005), and a buffer kit for SDS-PAGE (06-0301), at 18 mA/90 min. After the electrophoresis, the gel was stained with a Coomassie brilliant blue R-250 solution (0.1% Coomassie brilliant blue R-250, 40% methanol, and 10% acetic acid), and decolorized with a decoloring solution (10% methanol and 7.5% acetic acid) to detect proteins. An LMW Marker Kit (17-0446-01; Amersham Bioscience) was used as a molecular weight marker.

As a result, transformants in which an expression of a 25 kDa protein was enhanced were found, and it was confirmed that the desired cellulase was produced in the transformants. Among the transformants, strains K215-40, K215-42, and K229-72 were selected as the transformants producing the cellulase A162P, K166E, and APKE, respectively, and were used in further analysis. Further, the original cellulase NCE5 described in WO01/90375 was used as a control.

Example 3

Evaluation of Cellulases Obtained by Each Transformant

Culture supernatants obtained by cultivating *Humicola insolens* transformants K215-40, K215-42, and K229-72 in the (N) medium at 37° C. for 5 days were used to measure an EGU activity in three experimental groups, that is, (1) pH 6.0, (2) pH 6.0 and addition of 200 ppm sodium linear alkyl benzene sulfonate (LAS), and (3) pH 10.0.

The EGU activity was measured in accordance with the following procedures. Carboxymethyl cellulose (Hercules) was dissolved in an appropriate buffer to a final concentration of 3.5% as a substrate solution. That is, a substrate solution for the measurement at pH 6.0 was prepared by dissolving the substrate in a 0.1 mol/L phosphate buffer (pH 6.0), and a substrate solution for the measurement at pH 10.0 was prepared by dissolving the substrate in a 0.1 mol/L Tris-HCl buffer (pH 10.0). After 5 mL of each substrate solution was added to a test tube, each test tube was preheated in a water bath at 40° C. for 10 minutes. To the test tube, 0.15 mL of each test solution was added and the whole was mixed well to start an enzyme reaction at 40° C. After the reaction was carried out for 30 minutes, a viscosity of each reaction solution was measured by an R-type viscometer (RE 100; Toki Sangyo) in which the temperature was set at 40° C. An amount of enzyme which reduces the initial viscosity to ½ under each enzyme reaction condition is defined as "1 unit (U)". In Table 1, enzyme activities in the experimental groups (2) and (3) are shown as relative values when enzyme activities in the experimental group (1) are regarded as 100%.

TABLE 1

| Test sample | Experimental group | | |
| --- | --- | --- | --- |
| | (1) | (2) | (3) |
| K215-30 (A162P) | 100 | 26.6 | 29.6 |
| K215-42 (K166E) | 100 | 26.7 | 29.5 |
| K229-72 (APKE) | 100 | 21.1 | 36.6 |
| NCE (original cellulase) | 100 | 7.6 | 21.5 |

As shown in Table 1, it was found that each cellulase (A162P, K166E, and APKE) was resistant to LAS and maintained a high activity under alkaline conditions, in comparison with the original cellulase.

As a result, on comparison of the original cellulase, it was found that the each cellulase (A162P, K166E, and APKE) had a resistance to the LAS and a high activity under alkaline conditions.

INDUSTRIAL APPLICABILITY

The novel cellulase of the present invention is resistant to surfactants and exhibits a higher activity under alkaline conditions, in comparison with the original cellulose, and thus is useful as an active ingredient of a detergent for clothing.

Free Text in Sequence Listing

Each amino acid sequence of SEQ ID NOS: 3 to 5 is that of a cellulase resistant to surfactants. Each nucleotide sequence of SEQ ID NOS: 6 and 7 is a primer for site-directed mutagenesis.

Although the present invention has been described with reference to specific embodiments, various changes and modifications obvious to those skilled in the art are possible without departing from the scope of the appended claims.

The invention claimed is:

1. A polypeptide selected from the group consisting of:
   (a) a polypeptide comprising the amino acid sequence of SEQ ID NO:1, wherein said polypeptide has an amino acid substitution at position 162 of SEQ ID NO:1,
   (b) a polypeptide comprising the amino acid sequence of SEQ ID NO: 1, wherein said polypeptide has one additional amino acid at the N-terminus of said polypeptide, and wherein said polypeptide has an amino acid substitution at position 162 of SEQ ID NO:1,
   (c) a polypeptide comprising the amino acid sequence of SEQ ID NO: 1, wherein said polypeptide has a deletion of the N-terminal amino acid of said polypeptide, and wherein said polypeptide has an amino acid substitution at position 162 of SEQ ID NO:1, and
   (d) a polypeptide comprising the amino acid sequence of SEQ ID NO: 1, wherein said polypeptide has a plurality of additional amino acids at the N-terminus of said polypeptide, and wherein said polypeptide has an amino acid substitution at position 162 of SEQ ID NO:1.

2. The polypeptide according to claim 1, wherein said polypeptide comprises the amino acid sequence of SEQ ID NO: 3.

3. A cellulase composition comprising the polypeptide according to claim 1 and one or more members selected from the group consisting of a filler, an antiseptic and a nonionic surfactant.

4. A washing composition comprising the polypeptide according to claim 1 and one or more members selected from the group consisting of a surfactant, a bleach, a tarnish inhibitor, a soil release polymer, a second enzyme, an enzyme stabilizer, an optical brightener and a foaming agent.

5. A method of treating a cellulose-containing fabric, comprising contacting a cellulose-containing fabric with the polypeptide according to claim 1.

6. A method of reducing fuzzing of a cellulose-containing fabric or reducing a rate of the formation of fuzz, comprising contacting a cellulose-containing fabric with the polypeptide according to claim 1.

7. A method of color clarification of a colored cellulose-containing fabric, comprising contacting a colored cellulose-containing fabric with the polypeptide according to claim 1.

8. A method of reducing stiffness of a cellulose-containing fabric or reducing a rate of the formation of stiffness, comprising contacting a cellulose-containing fabric with the polypeptide according to claim 1.

9. The method according to claim 5, wherein the cellulose-containing fabric is contacted with the polypeptide according to claim 1 by soaking, washing, or rinsing the fabric in the presence of the polypeptide according to claim 1.

10. A method of de-inking waste paper, comprising contacting waste paper in need of de-inking with the polypeptide according to claim 1.

11. A method of improving freeness of paper pulp, comprising contacting paper pulp with the polypeptide according to claim 1.

12. A method of improving digestibility of animal feed, comprising treating animal feed with the polypeptide according to claim 1.

13. The polypeptide according to claim 1, wherein the amino acid at position 162 is substituted with proline.

14. The polypeptide according to claim 1, wherein said polypeptide consists of the amino acid sequence of SEQ ID NO: 3.

* * * * *